(12) United States Patent
Oren

(10) Patent No.: US 8,546,619 B2
(45) Date of Patent: Oct. 1, 2013

(54) PROCESS FOR THE PREPARATION OF BRONOPOL

(75) Inventor: Jacob Oren, Nesher (IL)

(73) Assignee: Bromine Compounds Ltd., Be'er Sheva (IL)

( * ) Notice: Subject to any disclaimer, the term of this patent is extended or adjusted under 35 U.S.C. 154(b) by 252 days.

(21) Appl. No.: 12/735,886

(22) PCT Filed: Feb. 26, 2009

(86) PCT No.: PCT/IL2009/000218
§ 371 (c)(1),
(2), (4) Date: Nov. 15, 2010

(87) PCT Pub. No.: WO2009/107133
PCT Pub. Date: Sep. 3, 2009

(65) Prior Publication Data
US 2011/0065964 A1 Mar. 17, 2011

Related U.S. Application Data

(60) Provisional application No. 61/064,328, filed on Feb. 28, 2008.

(51) Int. Cl.
C07C 201/12 (2006.01)
C07C 205/08 (2006.01)

(52) U.S. Cl.
USPC .............................. 568/712; 568/846; 568/946

(58) Field of Classification Search
None
See application file for complete search history.

(56) References Cited

U.S. PATENT DOCUMENTS 3,711,561 A 1/1973 Wessendorf

FOREIGN PATENT DOCUMENTS

| CN | 1903830 A | * | 1/2007 |
| DE | 1 804 068 | | 9/1970 |
| JP | 06293710 A | * | 10/1994 |

OTHER PUBLICATIONS

Complete English translation of JP 06293710A prepared by USPTO on Nov. 14, 2012.*
Machine English translation of CN 1903830 A generated by Dialog Oct. 19, 2012.*
Corrected complete translation of JP 06293710A prepared by USPTO on Nov. 14, 2012.*
International Search Report for PCT/IL2009/000218, mailed Jun. 23, 2009.
Written Opinion for PCT/IL2009/000218, mailed Jun. 23, 2009.

* cited by examiner

Primary Examiner — Brian J Davis
(74) Attorney, Agent, or Firm — Nixon & Vanderhye P.C.

(57) ABSTRACT

The invention provides a process for preparing bronopol, which process comprises charging a reaction vessel with water, bromopicrin, nitromethane and paraformaldehyde, gradually feeding a base into said reaction vessel under stirring, bringing the reaction to completion and separating bronopol from the aqueous reaction mixture.

10 Claims, 1 Drawing Sheet

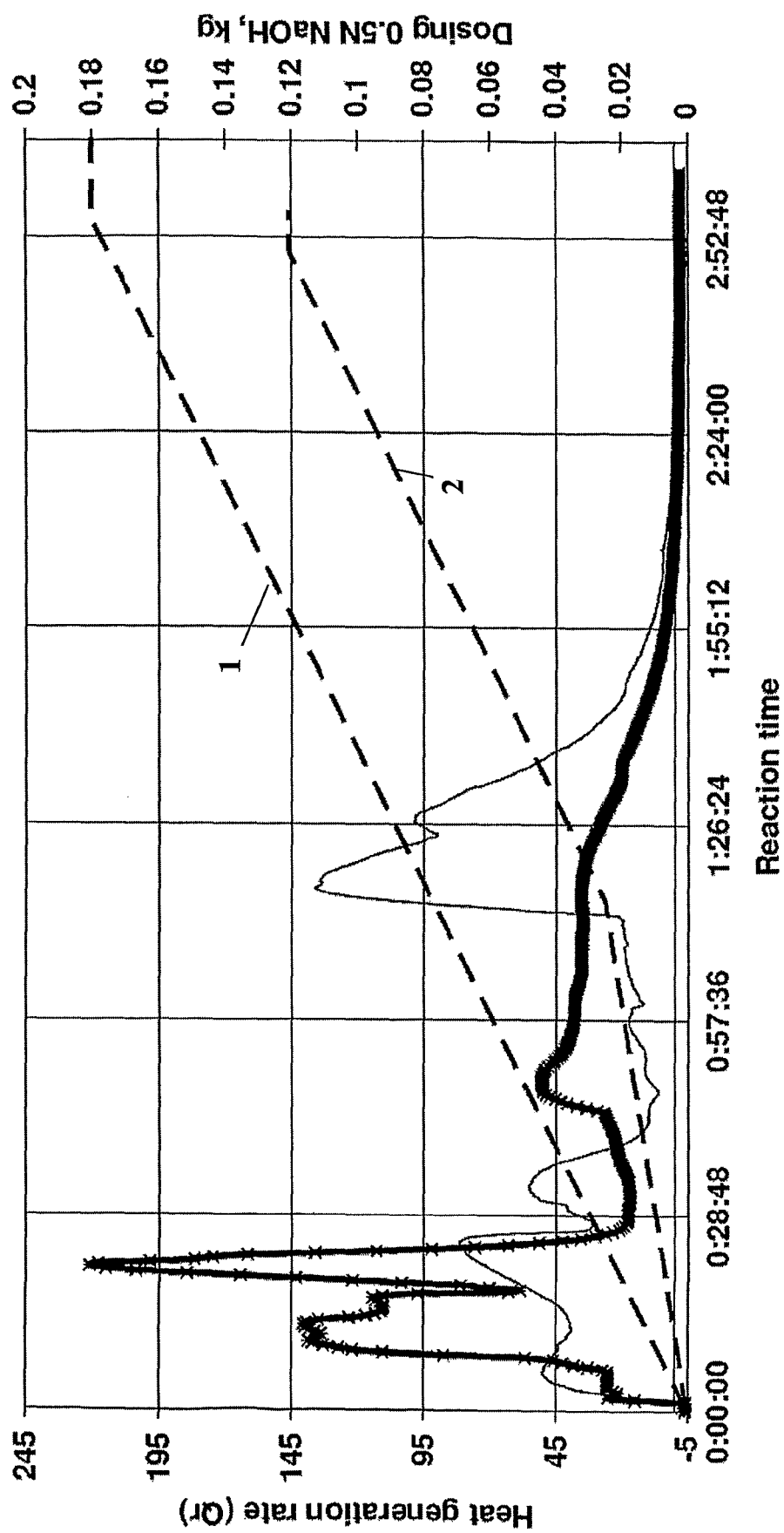

PROCESS FOR THE PREPARATION OF BRONOPOL

This application is the U.S. national phase of International Application No. PCT/IL2009/000218 filed 26 Feb. 2009, which designated the U.S. and claims priority to U.S. Application No. 61/064,328, filed 28 Feb. 2008, the entire contents of each of which are hereby incorporated by reference.

2-bromo-2-nitro-1,3-propanediol, also known as bronopol, has the following formula:

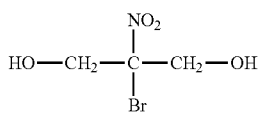

Bronopol is an antimicrobial agent used, inter alia, in the cosmetic industry and in the treatment of industrial waste water.

In their most general form, the conventional synthetic routes for preparing bronopol, starting from nitromethane ($CH_3NO_2$), can be represented by the following scheme:

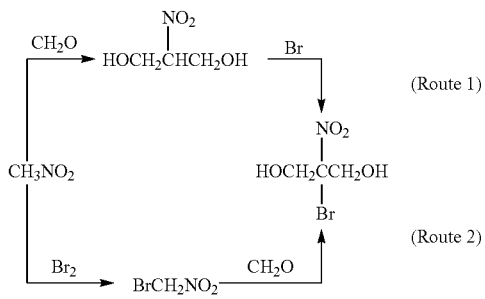

The first route involves the hydroxymethylation of nitromethane, to give 2-nitro-1,3-propanediol, followed by the bromination of said intermediate to give bronopol. According to the second route, the aforementioned sequence of reactions is applied in a reverse order, such that nitromethane is first brominated and the intermediate obtained is subsequently subjected to hydroxymethylation.

The present invention relates to the preparation of bronopol using tribromonitromethane ($CBr_3NO_2$, also known as bromopicrin; abbreviated BP). More specifically, the invention relates to the base-catalyzed reaction of bromopicrin, nitromethane and formaldehyde to give bronopol, as shown by the following reaction scheme (in which sodium hydroxide is indicated as a possible base):

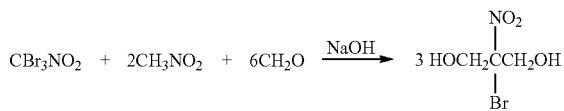

The use of bromopicrin in the preparation of bronopol according to the reaction scheme depicted above was described in JP 06-293710 and CN 1903830. However, it has been found that the aforementioned reaction is very exothermic and cannot be easily run in a controllable manner. The process provided by the present invention is especially aimed at solving certain problems associated with the strong heat released by said base-catalyzed reaction.

It has been found by the inventor that the rate of the reaction, and the rate of the evolution of heat by the reaction, may be favorably modified by adjusting one or more of the following factors:

(i) the formaldehyde reagent consumed during the reaction; or
(ii) the total amount and concentration of the base used for catalyzing the reaction; or
(iii) the scheme of feeding the base into the reaction mixture, especially the rate of addition, temperature and pH of the reaction mixture during the feeding.

According to one aspect, the process provided by the present invention for preparing bronopol comprises charging a reaction vessel with water, bromopicrin, nitromethane and paraformaldehyde, gradually feeding a base into said reaction vessel under stirring, bringing the reaction to completion and separating bronopol from the aqueous reaction mixture.

More specifically, bromopicrin, nitromethane and paraformaldehyde are reacted in an aqueous medium, in the presence of a catalytic amount of a base, wherein the base is preferably selected from the group consisting of alkali hydroxides and alkali carbonates, with sodium hydroxide and sodium carbonate being especially preferred. Water, and the reactants indicated above (in approximately stoichiometric amounts), are introduced into the reaction vessel, the reaction mixture is heated and an aqueous solution of the base (preferably a relatively dilute solution) is added gradually thereto, whereby the reaction is effectively controlled.

The bromopicrin starting material can be prepared by various synthetic routes. For example, bromopicrin may be conveniently produced according to the procedures described in WO 2007/023496 and WO 2008/146277. The relevant reaction is represented by the following chemical equation:

$$CH_3NO_2 + 3Br_2 + 3MOH \rightarrow CBr_3NO_2 + 3MBr + 3H_2O$$

Wherein M is an alkali metal, preferably sodium. Bromopicrin is obtained by charging a reaction vessel with water, nitromethane and bromine, followed by the gradual addition of a concentrated aqueous base (NaOH) solution. Especially preferred conditions for the preparation of the bromopicrin starting material according to the reaction depicted above (wherein the process is run in a batch mode), are as follows:
Temperature in the reactor: 40° C. (±5)
$Br_2$/Nitromethane molar ratio: 3.25 (±0.05)
Concentration of aqueous NaOH: 35% w/w (±1)
NaOH/Nitromethane molar ratio: 3.50 (±0.1)
Reaction time (time of addition of base): 4-6 h The reaction to give the bromopicrin starting material proceeds according to the rate of addition of the base. The reaction is exothermic, fast, and stops immediately after completing the feed of the base. The end of the reaction may be determined by the disappearance of the bromine and an increase in the pH in the reaction mixture from 6 to 9. After the end of the addition of the base, the reaction mixture is brought to room temperature (~25° C.) and the stirring is stopped. Upon completion of the reaction, two phases are obtained. The reaction mixture is separated into an aqueous phase and an organic phase, with the latter consisting essentially of the bromopicrin. The selectivity of the reaction to bromopicrin is more than 99% and the yield is about 97%, based on nitromethane. A complete preparative procedure illustrating the obtainment of the bromopicrin starting material is provided below.

Nitromethane to be used as a starting material according to the invention is commercially available. Nitromethane may be used in a slight molar excess relative to the bromopicrin starting material. More specifically, the molar ratio nitromethane:bromopicrin may be in the range between 2:1 and 2.05:1, preferably around 2.03:1.

The formaldehyde used in the process is generated in-situ in the reaction vessel from paraformaldehyde, which is a high molecular weight solid polymer represented by the formula: $HOCH_2(OCH_2)_{n-2}OCH_2OH$, wherein n indicates the degree of polymerization. The solid paraformaldehyde gradually dissolves in the reaction mixture upon heating in an alkaline environment, undergoing de-polymerization to give the formaldehyde which participates in the reaction. The gradual generation of the formaldehyde in the reaction vessel slows the rate of development of the reaction heat, as compared to the relatively fast heat release observed when aqueous formaldehyde is employed.

Paraformaldehyde suitable for use according to the invention may be in the form of fine powder, flakes or prills. The particulate form of the paraformaldehyde should be capable of providing the formaldehyde as consumed by the reaction. For example, paraformaldehyde with a degree of polymerization (n) in the range between 10 and 30, and assay, as formaldehyde, of about 95%, may be utilized in the process. Generally, the molar ratio between paraformaldehyde and bromopicrin is approximately stoichiometric, namely, around 6:1. A slight excess of paraformaldyde may be employed, for example up to about 6.1:1.

Water and the reagents listed above, namely, bromopicrin, nitromethane and paraformaldehyde, are charged to a reaction vessel, typically at room temperature. In general, the amount of water introduced at this stage into the reaction vessel is adjusted in order to allow, upon completion of the reaction, the obtainment of an aqueous solution in which the bronopol concentration is about 50-60 (w/w). It is noted that the base is generally used in the form of an aqueous solution, contributing water to the aqueous reaction mixture. More specifically, the concentration of the bromopicrin starting material in the reaction mixture before the addition of the base is preferably in the range between 33-37% w/w.

It is noted that prior to the commencement of the reaction, i.e., before the addition of the base into the reaction vessel, the reaction mixture comprises three phases and thus vigorous stirring is required in order to assure an effective mixing of the reagents. To this end, suitable agitators (e.g., an anchor-type stirrer) or impellers are mounted in the reaction vessel and are operated with a rotation speed in the range of 100 to 500 revolutions per minute (rpm). On a commercial scale production, it may be possible to use a more complex agitation arrangement to provide efficient mixing and effective heat and mass transfer.

Having charged the reaction vessel with water, bromopicrin and nitromethane as described above, the reaction vessel is heated, preferably to about 35-40° C. and the feeding of the base is allowed to start. It should be noted that the nitromethane starting material and the base are preferably sequentially charged into the reaction zone, such that the addition of the base succeeds the addition of the nitromethane. The reverse order of addition, namely, the case wherein the last reactant added to the reaction vessel is nitromethane, instead of the base, has been found to be less favorable from selectivity and efficacy perspectives. More specifically, the consumption of the base is higher and the selectivity of the reaction to bronopol is lower, with the amount of tris(hydroxymethyl)nitromethane (THMNM) by-product formed being considerably higher (the reaction mixture comprises less than 3% of said by-product when the addition of the base follows the addition of the nitromethane; when the reverse order of addition is applied, the level of the THMNM by-product increases to about 8%).

The molar ratio between the total amount of the base catalyst (e.g., sodium hydroxide) introduced into the reaction zone and the bromopicrin starting material is in the range of 1:100-10:100, and more preferably in the range of 3:100-7:100, and most preferably in the range between 4:100 and 6:100. It has been found that it is preferable, from a heat control perspective, to deliver the base to the reaction zone by means of an aqueous solution, in which the concentration of the base is preferably between 0.1 and 1.25N, and more preferably between 0.1 and 1N, and most preferably between 0.2 and 0.5N. In the case of an aqueous sodium hydroxide solution, the last two ranges are translated to 0.4-4 wt % and 0.8-2 wt %, respectively. In general, an aqueous sodium hydroxide solution in which the weight concentration of the base is between about 0.9 and 2.0%, and more specifically between 0.9 and 1.5% is considered sufficiently effective from selectivity, yield and heat control perspectives. Aqueous sodium hydroxide having a concentration of 1% is especially preferred.

In its most general form, the reaction proceeds under stirring, preferably at a temperature in the range between 35 and 60° C., preferably for 1-8 hours, more preferably for not less than 2 hours, even more preferably for not less than 3 hours, for example, for about 3-7 hours, specifically for about 4-5 hours. The duration of the reaction may vary according to the rate of addition of the base and the removal of heat from the reaction mixture. It is especially preferred to feed at least a portion of the base (at least 30%, and preferably between 50-100% of the total amount of the base) to the reaction mixture, wherein the temperature in the reaction mixture is above 41° C., e.g., between 45 and 60° C., and more preferably between 45 and 55° C. It has been found that feeding a relatively dilute aqueous base solution as set forth above, while maintaining the temperature of the reaction within the range indicated above, allows the reaction to reach completion with a moderate base consumption.

Several characteristics of the reaction profile, and several preferred modes for carrying out the reaction in a controllable manner, allowing a moderate heat release, are now described in more detail.

High performance liquid chromatography (HPLC) analysis of the reaction mixture during the addition of the base indicates that the reaction proceeds through the 2,2-dibromo-2-nitroethanol (DBNE) intermediate, as shown by the following scheme (in which the base employed is represented by aqueous sodium hydroxide):

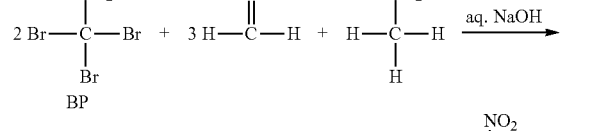
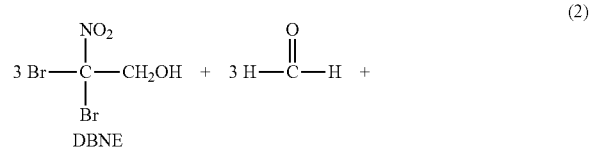

-continued

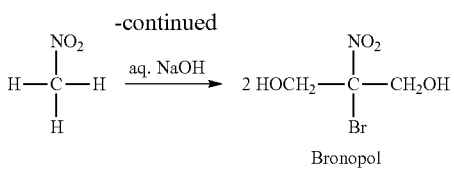
Bronopol

It has been found that after the addition of less than 25% of the total amount of the base, and more specifically, after about 10-20% of the total amount (approximately 15%), the bromopicrin is almost completely reacted and the intermediate, 2,2-dibromo-2-nitroethanol (DBNE), is formed. The formation of bronopol begins approximately at this stage. After the addition of a further portion of the base (between about 15 and 25%, more specifically 20%, such that the accumulated amount of base in the reaction mixture is about 28-43%, and more specifically about 35%), more than 50% of the bronopol (about 60-70%) is formed. At this point, there is a reduction in the rate of heat release. During the addition of the remaining aqueous base solution, the reaction to form bronopol is completed and the reaction mixture changes into a homogeneous solution.

It has been observed that the rate of heat evolved by the reaction during the addition of the base is not constant over time. More than 60% of the total heat, and more specifically, about 70-80% of the total heat generated by the reaction, is released during the addition of less than one third, and even less than one quarter of the total amount of the base. The remaining heat (about 20-30%) is gradually and decreasingly released, to the end of the base feeding.

It has also been found that if a considerable portion of the base (about 50-75%) is added to the reaction mixture at a temperature below 40° C., i.e., at about 35-38° C., then the reaction does not reach completion under the said temperature and feeding regime. Even subsequent heating of the reaction mixture to about 50° C. does not bring the reaction to completion. Feeding a considerable portion of the base to the reaction mixture at a temperature below 40° C. increases the overall consumption of the base, such that a large amount of base is ultimately required in order to assure the completion of the reaction and the obtainment of bronopol in a satisfactory selectivity of not less than 90%, and preferably not less than 93%.

The invention accordingly provides a process for preparing bronopol, which process comprises charging a reaction vessel with water, bromopicrin, nitromethane and formaldehyde source (preferably in the form of paraformaldehyde), gradually feeding a base into said reaction vessel under stirring, maintaining, during said feeding, a time-temperature-pH profile whereby the selectivity of the reaction to bronopol is maximized while the amount of the base employed is minimized, and separating bronopol from the aqueous reaction mixture.

Several feeding schemes of the base may be employed in order to maintain the desired time-temperature-pH profile in the reaction mixture, such that the selectivity of the reaction is preferably not less than 90% (HPLC, area %), more preferably not less than 93%, e.g., between 93-97%, with a low base consumption, preferably in the range between 3-7 mol %, more preferably 4-6 mol %, relative to the bromopicrin starting material. The gradual feeding schemes to be employed are such that the time-temperature-pH profile of the reaction includes feeding at least a portion of the base at a temperature above 41° C., more specifically between 41 and 60° C., preferably between 45 and 55° C., while the pH of the reaction mixture is kept within the range between 6 and 8.

According to one possible feeding scheme, an aqueous solution of the base, having a concentration in the range between 0.1 and 1N, is fed to the reaction mixture at a substantially constant rate during a period of not less than 2 hours, preferably not less than 3 hours, more preferably between 3 to 7 hours, and even more preferably between 4 to 5 hours, wherein during at least a portion of said feeding period, and possibly during the entire feeding period, the temperature in the reaction mixture is above 41° C., more preferably above 44° C., and most preferably between 45 and 55° C. By the term "substantially constant rate" is meant that the total amount of the base is uniformly supplied to the reaction mixture during the reaction period, with short intermissions, if necessary, in order to prevent overheating of the reaction mass, namely, increasing the reaction time. When an aqueous solution of a base with a concentration between 0.2 and 1N is used, such as sodium hydroxide solution with a concentration in the range between 0.8 and 4.0 wt %, then at least 30%, and preferably between 50-100% of the total amount of the base can be added to the reaction mixture at a temperature in the range between 41 and 55° C., over a period of time of not less than 3 hours (3-7 hours). Such a feeding scheme has been found effective in preventing the overheating of the reaction mixture, allowing the reaction to proceed smoothly with an acceptable heat removal rate, excellent selectivity and low base consumption, e.g., between 3-7 mol % relative to the bromopicrin starting material.

According to another possible feeding scheme, the rate of addition of the base to the reaction mixture is not kept constant during the reaction; the rate of addition is increased during the progress of the reaction. Thus, the gradual feeding of the base into the reaction vessel comprises switching from a first feeding rate to a second, increased, feeding rate.

The switching from the first, relatively slow feeding rate to the second, relatively fast feeding rate, is carried out after the completion of the first stage of the reaction, namely, after the obtainment of the 2,2-dibromo-2-nitroethanol (DBNE) intermediate. As already indicated above, the first stage of the reaction, from bromopicrin to 2,2-dibromo-2-nitroethanol (DBNE) is fast, and a relatively small quantity of base (10-20%), and lower temperature, is required than the second stage, from DBNE to bronopol. The first stage of the reaction is accompanied by an extensive heat release. During the first stage, the base is carefully added at a slow rate, restraining the rate of heat release. Having completed the first, highly exothermic stage of the reaction (the time-temperature profile of the reaction exhibits a sharp peak indicative of the completion of the first stage of the reaction), the remaining amount of the base may be fed at an increased rate, with the temperature in the reaction mixture being maintained at about 45-55° C. Under these conditions, the selectivity to bronopol at the end of the addition of the base is approximately 95%, with the amount of base consumed being fairly small (between 3-7 mol % relative to the bromopicrin starting material). A second, less sharp exothermic peak, followed by the obtainment of a clear solution, is indicative of the essentially complete formation of bronopol.

A preferred mode of practicing the gradual feeding of the base into said reaction vessel as described above, namely, employing a non-constant feeding rate, comprises feeding a first quantity of the base to the reaction mixture at a first rate, said first quantity being preferably not more than 40%, more specifically between to 30% of the total amount of the base, and subsequently feeding a second quantity of the base to the reaction mixture at second rate, wherein the first rate is slower, e.g., 2-5, preferably 3-4 fold slower, than the second rate. The first feeding rate is employed while the temperature of the reaction mixture is between 35 and 45° C., whereas the second, increased feeding rate is employed with the temperature of the reaction being in the range between 45 and 55° C., the reaction being brought to completion at a temperature in the range between 45 and 55° C. Under this feeding scheme, the reaction may be finished after 3 to 7 hours, with a selectivity of 93-95%, and a base consumption of less than 7 mol % relative to the bromopicrin starting material.

As indicated above, the method of the present invention may be practiced by feeding the base at a constant rate, using a dilute aqueous solution of the base, with intermissions during the feeding intended to prevent overheating, such that the reaction time is preferably between 3 and 7 hours. However, in certain cases, it may be advantageous to prefer the non-constant base feeding rate method set forth above over the constant feeding rate method. FIG. 1 illustrates the advantage associated with the non-constant base feeding rate. In the graph, the abscissa indicates the reaction time (hours), the left ordinate indicates the heat generation rate and the right ordinate indicates the amount of base fed to the reaction mixture (0.5N NaOH solution). The experiment was carried in RC1 reactor with 1.5 mole BP. The dotted lines represent the amount of base added to the reaction mixture as a function of time, for two distinct feeding schemes. The dotted line indicated by numeral 1 corresponds to the feeding of the base under a constant rate, as evident by the slope of said line. The dotted line indicated by numeral 2 is characterized by two different slopes, indicative of a switching from a first, relatively slow feeding rate to a faster rate (the switching occurred about 75 minutes after the start of the reaction; the feeding rate employed after 75 minutes is equal to the feeding rate according to line 1). The continuous lines represent the rate of heat generated by the reaction as a function of time under the two feeding methods set forth above. The thick and thin continuous lines represent the heat generation rate under the constant base feeding rate method (line 1) and the non-constant base feeding rate method (line 2), respectively. The heat generation rate for the reaction is a function of the dosing rate of the 0.5N NaOH and the reaction time. As shown in the graph, during the first stage of the reaction, the heat generation rate strongly depends on the base dosing rate. More specifically, the thick continuous line exhibits two sharp peaks already within the first 30 minutes from the start of the reaction, indicating that a considerable amount of the heat generated by the reaction is released within a short period. As clearly shown in the graph, the non-constant base feeding rate allows the heat to be more evenly released during the reaction, reducing the risk of a rapid temperature raise in the reaction mixture. Notably, the feeding scheme involving the switching from a first, relatively slow feeding rate to a second, faster rate also allows a considerable reduction in the total base consumption (approximately 30%).

It has been found that the presence of a small amount of bronopol (between about 1 and 10% mol of the bronopol) in the reaction mixture before the start of the addition of the base moderates the change in the rate of heat release, although there is a slight slow-down in the rate of the reaction and more base is required (about 5 to 15% more than usual, namely, between about 6-7 mol % relative to the bromopicrin starting material) to complete the reaction.

The concentration of the product present in the final reaction mixture is in the range of 50 and 60% (w/w). The product is isolated from the reaction mixture by cooling the same to about 0 and 20° C., whereby bronopol crystallizes from the reaction mixture (the crystallization may be induced by means of seeding). The solid product is readily separable from the liquid phase, e.g., by filtration, in a purity of not less than 99.0%. The direct yield of the process is about 70-80%, and more specifically around 75%.

A useful procedure for the isolation of the product from the reaction mixture involves cooling the reaction mixture at a rate of about 0.3-0.5° C. per minute, whereby a slurry of bronopol in water is formed. During the cooling, an oversaturated solution is obtained and the addition of a small amount of pure bronopol (about 1 g per 1 mol starting BP) to the reaction vessel at about 35° C. induces the crystallization of the bronopol. The crystallization stage is complete when the temperature in the reaction vessel reaches 7° C.

Having separated the solid product from the liquid phase by means of filtration, the product is washed, preferably using cold water (at about 10° C.) in an amount of 200-400 g, more preferably 250-350 g, per kg of the bronopol product. The washed product is finally dried, for example in a rotary evaporator at a vacuum of 20-30 mmHg, starting at 25° C.-50° C. for 2 h, followed by a further drying at 50-70° C. for 1 h, to constant weight.

As already indicated above, the bronopol obtained is of high purity. The preferred purity level of the product is in the range between 99.5 and 99.9% (by HPLC, area %), with a melting point in the range between 131 and 133° C., more preferably between 132 and 133° C. The improved purity profile indicated above is directly attainable by the process, without the need to apply re-crystallization procedures.

The aqueous liquid phase obtained following the separation of the product may be treated in order to recover further crops of the product. To this end, the aqueous liquid phase is concentrated by partial evaporation to approximately one third of the original weight of the liquid phase. The residue obtained is cooled, and the bronopol which crystallizes is collected by filtration. The purity of this second crop (96-99%) is higher than the selectivity of the reaction (93-95%) and it is charged into the reaction mixture of a subsequent reaction followed by the crystallization procedure as describe above. The total yield of the product accordingly is increased to more than 80%, more specifically between 83-90%.

The following is a description of the analytical procedures used.

The Purity and Assay of Bronopol was Determined by HPLC.
HPLC analysis methods of bronopol: Purity check and Assay
HPLC Purity Check (Gradient)
Column and packing: Kromasil C18, 250*2.1 mm, 5 μm
Solvents: A: $H_2O(KH_2PO_4$ 2.7 g/L, pH=4); B: AcN
Gradient Program

| Time | A | B |
| --- | --- | --- |
| 0 | 85 | 15 |
| 5 | 85 | 15 |
| 15 | 50 | 50 |
| 20 | 50 | 50 |
| 22 | 85 | 15 |

Post time: 10 min
Flow rate: 0.22 ml/min
Detector: 210 nm
Injection volume: 10 μL
Sample preparation: 200 mg sample in 100 ml measuring bottle, ($KH_2PO_4$ 2.7 g/L, $H_2O$, pH=4)
HPLC Assay (Isocratic)
Column and packing: Kromasil C18, 250*4.6 mm, 5 μm
Solvents: A: $H_2O(KH_2PO_4$ 2.7 g/L, pH=4)—85%;
B: AcN—15%

Flow rate: 1 ml/min
Detector: 220 nm
Injection volume: 20 μL
Oven temperature: 25° C.
Standard preparation: 100 mg standard in 100 ml measuring bottle, ($KH_2PO_4$ 2.7 g/L, pH=4)
Sample preparation: 100 mg sample in 100 ml measuring bottle, ($KH_2PO_4$ 2.7 g/L, pH=4)
Analysis time: 15 min The melting point (m.p.) of bronopol was measured on an Optimelt MPA 100 instrument.

BRIEF DESCRIPTION OF THE DRAWINGS

FIG. 1 illustrates a comparison between reactions carried out with constant and non-constant feeding rates of the base.

EXAMPLES

In the examples, the following abbreviations are sometimes used: aq.—aqueous; bromopicrin—BP; bronopol—BRP; density—d; not analysed—n.a.; not detected—n.d.; nitromethane—NM; paraformaldehyde—PFAL; room temperature—RT; ~ indicates about.

Example 1

Preparation of the Bromopicrin Starting Material

Into a 1 L jacketed reactor equipped with a mechanical stirrer, condenser, thermocouple and peristaltic pump for the addition of aq. NaOH solution, were introduced water (160 g), nitromethane (100 g) and bromine (845 g), at room temperature and under stirring. Aq. 34.7% NaOH (655 g) was added to the reactor at a rate of 164 g/h. The temperature in the reactor remained at 36-41° C. throughout the addition (the set point of the Lauda was 35-36° C.) The end of the addition was determined by the disappearance of the colour of the bromine and an increase in the pH of the reaction mixture from 6 to 9.

The mixture obtained was stirred for 0.5 h at 41→24° C. (the set point of the Lauda was 20° C.). The stirring was then stopped and two phases were obtained. The heavy organic phase (474 g) was bromopicrin in a purity of >99% (GC, area %) and a yield of 97.1%, based on nitromethane.

The aqueous phase (1270 g) can be treated to obtain aq. 42-44% NaBr solution or aq. HBr, or to recover the bromine.

Example 2

Preparation of Bronopol

Into a 1 L jacketed reactor equipped with a mechanical stirrer, condenser, thermocouple and peristaltic pump for the addition of aq. NaOH solution, were introduced water (200 g), paraformaldehyde (189 g), bromopicrin (290 g) and nitromethane (122 g), at room temperature and under stirring. The mixture was then heated to 45° C. and aq. 0.5N NaOH (100 g) was added dropwise into the reactor over 135 min. The temperature in the reactor remained at 45-48° C. throughout the addition. The pH of the reaction mixture went down from 8 to 6.

The mixture obtained was stirred for 1 h at ~50° C. then cooled to 14° C. and the crude bronopol crystallized out. The slurry was filtered and washed with water (150 g) at RT. The filtrate and wash (491 g) contained ~90 g bronopol.

The product was dried to constant weight in an evaporator, at RT→70° C. and a vacuum of 30 mm Hg. Crude bronopol (459 g) was obtained in a purity of >99.5% (HPLC).

Example 3

Preparation of Bronopol

Into a 1 L jacketed reactor equipped with a mechanical stirrer, condenser, thermocouple and peristaltic pump for the addition of aq. NaOH solution, were introduced water (328 g), bromopicrin (290 g), paraformaldehyde (192 g) and nitromethane (127 g), at room temperature and under stirring. The mixture was then heated to 45° C. and aq. 1N NaOH (63 g) was added dropwise to the reactor over 3 h. The temperature in the reactor remained at 45-53° C. throughout the addition. The pH of the reaction mixture went down from 8 to 6.

Wet bronopol from the second crop of a previous reaction (~90 g) was added and the mixture obtained was stirred for 30 min. at ~50° C. The mixture was then cooled to 15° C. and the crude bronopol crystallized out. The slurry was filtered and washed with water (170 g) at 15° C.

The product was dried to constant weight in an evaporator at RT→70° C. and a vacuum of 30 mm Hg. Crude bronopol (522 g) was obtained in a purity of >99.5% (HPLC).

The filtrate and wash from the crystallization (674 g) was partially evaporated at 30 mmHg (436 g water and lights removed). The evaporation residue was cooled to 20° C., filtered and washed with 50 g water. Wet bronopol (84 g) was obtained, and the filtrate (192 g) was discarded.

Example 4

Preparation of Bronopol

Into a 1 L jacketed reactor equipped with a mechanical stirrer, condenser, thermocouple and peristaltic pump for the addition of aq. NaOH solution, were introduced water (270 g), paraformaldehyde (189 g), bromopicrin (290 g) and nitromethane (122 g), at room temperature and under stirring. The mixture was then heated to 50° C. and aq. 0.5N NaOH (80 g) was added dropwise to the reactor in 2 portions: 25 g in 74 min., then 55 g in 96 min., then the mixture was stirred for 1 h at 50-52° C. The pH of the reaction mixture went down from 8 to 6.

Wet bronopol from a previous reaction (60 g) was added and the mixture obtained was stirred for 30 min. at ~50° C. The mixture was then cooled to 12° C. and the crude bronopol crystallized out. The slurry was filtered and washed with water (170 g) at 12° C.

The product was dried to constant weight in an evaporator at RT→70° C. and a vacuum of 30 mm Hg. Crude bronopol (509 g) was obtained in a purity of >99.5% (HPLC).

The filtrate and wash from the crystallization (607 g) was partially evaporated at 30 mmHg (398 g water and lights removed). The evaporation residue was cooled to 20° C., filtered and washed with 50 g water. Wet bronopol (73 g) was obtained, and the filtrate (163 g) was discarded.

Example 5

Preparation of Bronopol

Into a 1 L jacketed reactor equipped with a mechanical stirrer (anchor-type), condenser, thermocouple, pH meter and peristaltic pump for the addition of aq. NaOH solution, were introduced water (200 g), bromopicrin (298 g, 1 mol), nitromethane (123 g, 2.015 mol, Aldrich) and paraformaldehyde (189 g, 6 mol, Aldrich), at room temperature and under stirring.

The mixture was then heated to 44° C. and aq. 1% NaOH (200 g) was added dropwise to the reactor over 200 min. During the addition of the base, the temperature in the reactor did not rise above 55° C.

At the start of the addition of the aq. NaOH, the reaction mixture comprises three phases. The mixture was vigorously stirred (~400 rpm). At the end of the addition of base, a single liquid phase is obtained.

During the addition of the base, there was a gentle rise of the temperature in the reactor (44° C. to 51° C.), achieved by recycle of water in the reactor jacket. The set point (s.p.) of the Lauda was changed manually from 45→40→45° C. After the addition of 80 g of the basic solution, the rate of heat release leveled out and the s.p. in the heating-cooling Lauda was held at 50° C.

Monitoring of the pH showed a change in the range from 7.2→5.8→6.8. After the completion of the addition of the base, the reaction mixture was stirred for 60 min at 50° C. during which the pH fell from 6.8 to 5.3.

Two samples were taken for HPLC analysis, one 15 min after the end of the addition of the base, and the second 1 h after the end of the addition of the base. The results indicate that the reaction to obtain bronopol almost finished with the end of the addition of the base.

The mixture was then cooled to 5° C. over 90 min. Pure bronopol (1 g) was added to the reactor at 27° C. Crystallization started immediately and pure bronopol crystallized out. The slurry was filtered and washed with water (150 g) at 5-10° C.

The product was dried to constant weight in an evaporator at RT→70° C. and a vacuum of 30 mm Hg. Pure bronopol (461 g) was obtained in a purity of 99.9% by HPLC, area %, with an assay of 99.8% and m.p. 132-133° C.

The filtrate and wash from the crystallization (626 g) was partially evaporated at 30 mm Hg to remove water and lights (391 g). The evaporation residue (230 g) was cooled to 20° C., and crude product crystallized out. The slurry obtained was filtered and washed with water (50 g). Wet, crude bronopol (80 g) was obtained in a purity of more than 95% (HPLC, area %), and the filtrate (185 g) was discarded.

The direct yield of bronopol was 76.8%, and after recycle of the crude bronopol (second crop) from the filtrate in the crystallization stage to the next batch, the overall yield of the process was 86-88%.

Example 6

Preparation of Bronopol

Into a 1 L jacketed reactor equipped with a mechanical stirrer (anchor-type), condenser, thermocouple, pH meter and peristaltic pump for the addition of aq. NaOH solution, were introduced water (200 g), bromopicrin (298 g, 1 mol), nitromethane (123 g, 2.015 mol, Aldrich) and paraformaldehyde (189 g, 6 mol, Aldrich), at room temperature and under stirring.

The mixture was then heated to 44° C. and aq. 1% NaOH (200 g) was added dropwise to the reactor over 200 min: the first 65 g in 120 min and the remaining 135 g in 100 min. During the addition of the base, the temperature in the reactor did not rise above 55° C.

At the start of the addition of the aq. NaOH, the reaction mixture comprises three phases. The mixture was vigorously stirred (~400 rpm). At the end of the addition of the base, a single liquid phase is obtained.

During the addition of the base, there was a gentle rise of the temperature in the reactor (44° C. to 52° C.), achieved by recycle of water in the reactor jacket. The set point (s.p.) of the Lauda was 45° C. After the addition of 104 g of the basic solution, the rate of heat release leveled out and the s.p. in the heating-cooling Lauda was held at 50° C. Samples were taken for HPLC analysis during the addition of the base. The results indicate that the reaction to obtain bronopol finished with the end of the addition of the base.

The mixture was then cooled to 7° C. over 90 min. Pure bronopol (1 g) was added to the reactor at 34° C. Crystallization started immediately and pure bronopol crystallized out. The slurry was filtered and washed with water (150 g) at 5-10° C.

The product was dried to constant weight in an evaporator at RT→70° C. and a vacuum of 30 mm Hg. Pure bronopol (445 g) was obtained in a purity of 99.9% by HPLC, area %, with an assay of 100.4% and m.p. ~132° C.

The direct yield of bronopol was ~74%. After recycle of the crude bronopol (second crop) from the filtrate in the crystallization stage to the next batch, according to the procedures set forth in previous examples, the overall yield of the process increased to about 86-88%.

The change in the temperature and pH of the reaction mixture was monitored during the addition of the base, and the results are presented in the following table.

| Time min | aq. 1% NaOH g | s.p. ° C. | $T_R$ ° C. | pH |
|---|---|---|---|---|
| 0 | 0 | 45 | 44.1 | 3.1 |
| 14 | 4 | 45 | 47.0 | 7.1 |
| 31 | 8 | 45 | 48.0 | 7.6 |
| 43 | 19 | 45 | 48.9 | 7.3 |
| 46 | 20 | 45 | 48.5 | 7.2 |
| 52 | 27 | 45 | 48.9 | 6.7 |
| 62 | 30 | 45 | 52.2 | 7.1 |
| 69 | 34 | 45 | 48.6 | 7.4 |
| 86 | 46 | 45 | 49.2 | 7.3 |
| 93 | 49 | 45 | 48.5 | 7.5 |
| 109 | 56 | 45 | 47.6 | 7.6 |
| 120 | 65 | 45 | 47.4 | 7.6 |
| 132 | 97 | 45 | 47.4 | 7.3 |
| 146 | 104 | 50 | 46.0 | 7.2 |
| 161 | 123 | 50 | 49.2 | 7.0 |
| 176 | 144 | 50 | 50.2 | 6.9 |
| 198 | 162 | 50 | 50.2 | 6.4 |
| 220 | 200 | 50 | 50.0 | 7.1 |
| 265 | — | 50 | 50.3 | 5.5 | s.p.: set point
$T_R$: temperature in the reactor

Example 7

Preparation of Bronopol Using Aqueous Formaldehyde

Into a 1 L jacketed reactor equipped with a mechanical stirrer, condenser, thermocouple and peristaltic pump for the addition of aq. NaOH solution, were introduced bromopicrin (290 g), aq. 37% formaldehyde (520 g) and nitromethane (127 g), at room temperature and under stirring. The mixture was then heated to 45° C. and aq. 1N NaOH (61 g) was added dropwise to the reactor over 2.5 h. The temperature in the reactor was 45-64° C. throughout the addition. The pH of the reaction mixture went down from 8 to 6.

The mixture obtained was stirred for 30 min. at ~50° C. The mixture was then cooled to 15° C. and the crude bronopol crystallized out. The slurry was filtered and washed with water (170 g) at 15° C.

The product was dried to constant weight in an evaporator at RT→70° C. and a vacuum of 30 mm Hg. Crude bronopol (439 g) was obtained in a purity of ~99% (HPLC).

The filtrate and wash from the crystallization (674 g) was partially evaporated at 30 mmHg (455 g water and lights removed). The evaporation residue was cooled to 20° C., filtered and washed with 50 g water. Wet bronopol (84 g) was obtained, and the filtrate (167 g) was discarded.

Example 8 (Comparative)

Preparation of Bronopol at Different Temperatures

An experiment was carried out in which most of the base (75%) was added at a temperature of 35-38° C. From the results summarised in the table below, it can be seen that the reaction was incomplete, even after heating to 50° C. A larger amount of aqueous 1% NaOH had to be added (329 g instead of 200 g) to complete the reaction and to obtain bronopol in a selectivity of 94%.

| H$_2$O g | BP g | NM g | PFAL g | 1% NaOH g* | Temp °C. | Time min* | Composition, by HPLC, area % | | | |
|---|---|---|---|---|---|---|---|---|---|---|
| | | | | | | | THMNM | NM | BRP | DBNE |
| 200 | 298 | 123 | 189 | 115 | 44->54 | 120 | 1.0 | 6.1 | 85.6 | 7.2 |
| | | | | 155 | 50 | 156 | 2.3 | 1.5 | 93.3 | 2.8 |
| | | | | 200 | 50 | 200 | 2.7 | 0.7 | 94.6 | 2.0 |
| 200 | 298 | 123 | 189 | 150 | 35->38 | 150 | n.a. | n.a. | n.a. | n.a. |
| | | | | 200 | 45->51 | 200 | 0.3 | 30.9 | 34.2 | 32.0 |
| | | | | 308 | 50->51 | 270 | 1.5 | 2.3 | 92.4 | 3.4 |
| | | | | 329 | 50 | 300 | 2.2 | 1.1 | 94.0 | 2.2 |

Example 9 (Comparative)

Preparation of Bronopol by the Addition of the Nitromethane after the aq. NaOH

Into a 1 L jacketed reactor equipped with a mechanical stirrer, condenser, thermocouple and peristaltic pump for the addition of nitromethane, were introduced water (200 g), bromopicrin (290 g), paraformaldehyde (193 g) and aq. 0.5N NaOH solution (208 g), at room temperature and under stirring. The mixture was then heated to 47° C. and nitromethane (127 g) was added dropwise to the reactor over 4 h. The temperature in the reactor remained at 47-52° C. throughout the addition. The pH of the reaction mixture went down from 11 to 6. The conversion to bronopol was only 46%. To complete the reaction, 0.5N NaOH solution (43 g) was added. The mixture obtained was stirred for 50 min. at ~50° C. The mixture was then cooled to 7° C. and the crude bronopol crystallized out. The slurry was filtered and washed with water (170 g) at 5-10° C.

The product was dried to constant weight in an evaporator at RT→70° C. and a vacuum of 30 mm Hg. Crude bronopol (409 g) was obtained in a purity of 98.7% (HPLC).

Example 10

Preparation of Bronopol Using aq. Na$_2$CO$_3$ as Base

Into a 1 L jacketed reactor equipped with a mechanical stirrer, condenser, thermocouple and peristaltic pump for the addition of aq. base solution, were introduced water (200 g), bromopicrin (298 g), paraformaldehyde (194 g) and nitromethane (126 g), at room temperature and under stirring. The mixture was then heated to 45° C. and aq. 2.65% Na$_2$CO$_3$ (120 g) was added dropwise to the reactor over 3 h. The temperature in the reactor remained at 45-50° C. throughout the addition. The pH of the reaction mixture went down from 8 to 6.

The mixture obtained was stirred for 30 min. at ~50° C. The selectivity to bronopol was 95.2% (by HPLC, area %).

The invention claimed is:

1. A process for preparing bronopol, which process comprises charging a reaction vessel with water, bromopicrin, nitromethane and paraformaldehyde, gradually feeding a base into said reaction vessel under stirring, bringing the reaction to completion and separating bronopol from the aqueous reaction mixture.

2. A process according to claim 1 wherein the molar ratio between the total amount of the base fed into the reaction vessel and the bromopicrin is in the range of 1:100-10:100.

3. A process according to claim 2, wherein the base to bromopicrin ratio is in the range between 3:100 and 7:100.

4. A process according to claim 1, wherein the base is fed to the reaction vessel in the form of an aqueous solution, in which the concentration of the base is between 0.1 and 1.25N.

5. A process according to claim 4, wherein the base is provided as an aqueous solution with a concentration between 0.2 and 0.5N.

6. A process according to claim 5, wherein an aqueous solution of sodium hydroxide with a weight concentration in the range between 0.8 and 2% is used.

7. A process according to claim 1, wherein at least a portion of the base is fed while the temperature in the reaction mixture is above 41'C.

8. A process according to claim 7, wherein at least 30% of the total amount of the base is fed to the reaction mixture at a temperature in the range between 45 and 60° C.

9. A process according to claim 1, wherein the bromopicrin used is obtained by charging a reaction vessel with water, nitromethane and bromine, followed by the gradual addition of a concentrated aqueous base, and upon completion of the reaction, separating the reaction mixture into an aqueous phase and an organic phase.

10. A process according to claim 1, claims, wherein the bronopol is obtained in a purity of 99.5-99.9% (area), as indicated by HPLC analysis.

* * * * *